US00PP27396P3

(12) United States Plant Patent
Korlipara

(10) Patent No.: US PP27,396 P3
(45) Date of Patent: Nov. 15, 2016

(54) ***COREOPSIS* PLANT NAMED 'BUTTERMILK'**

(50) Latin Name: ***Coreopsis verticillata* hybrid**
Varietal Denomination: Buttermilk

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 95 days.

(21) Appl. No.: 14/544,791

(22) Filed: Feb. 18, 2015

(65) Prior Publication Data

US 2016/0242350 P1 Aug. 18, 2016

(51) Int. Cl.
*A01H 5/02* (2006.01)

(52) U.S. Cl.
USPC ..... Plt./417

(58) Field of Classification Search
USPC ..... Plt./417
See application file for complete search history.

(56) References Cited

PUBLICATIONS

American Nurseryman Commercial Horticulture's Authority for More Than a Century Woodies & Perennials 2015 New Plants, Dec. 2014, pp. 36-38.*

* cited by examiner

*Primary Examiner* — June Hwu
(74) *Attorney, Agent, or Firm* — Klarquist Sparkman, LLP

(57) ABSTRACT

A new and distinct *Coreopsis* plant named 'Buttermilk' characterized by numerous daisy-type inflorescences that grow to 3.5 cm in diameter, inflorescences that are light yellow, hardy to Zone 6, maybe lower, grass green foliage on short stems, flowering for the whole summer, a low, dense, mounding habit, and excellent vigor.

1 Drawing Sheet

Botanical denomination: *Coreopsis verticillata* hybrid.
Variety designation: 'Buttermilk'.

BACKGROUND OF THE INVENTION

The present invention relates to a new and distinct *Coreopsis* and given the cultivar name 'Buttermilk'. *Coreopsis* is in the family Asteraceae. This new cultivar originated from a controlled breeding program to produce hardy compact *Coreopsis*. The new cultivar originated from planned cross of two proprietary unnamed *Coreopsis verticillata* hybrid seedlings. The new cultivar of *Coreopsis* is an herbaceous perennial to be grown for landscape and container use in a sunny site.

Compared to the parents the new cultivar has light yellow flowers rather than yellow and/or a shorter habit.

Compared to *Coreopsis* 'Star Cluster', U.S. Plant Pat. No. 23,035, the new cultivar is denser in habit with more stems from the crown and better branching. The new cultivar has smaller flowers without a center dark star pattern.

SUMMARY OF THE INVENTION

The following traits have been repeatedly observed and are determined to be the unique characteristics of the new variety. These characteristics in combination distinguish *Coreopsis* 'Buttermilk' as a new and distinct cultivar:

1. numerous daisy-type inflorescences that grow to 3.5 cm in diameter,
2. inflorescences that are light yellow,
3. hardy to Zone 6, maybe lower,
4. deep green foliage on short stems, 5. flowering for the whole summer,
6. a low, dense, mounding habit, and
7. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a nine-month-old *Coreopsis* 'Buttermilk' growing in the ground in the trial field in July in Canby, Oreg.

FIG. 2 shows a three-month-old *Coreopsis* 'Buttermilk' growing in a gallon container (not shown) in full sun outside in Canby, Oreg.

DETAILED PLANT DESCRIPTION

The following is a detailed description of the new *Coreopsis* cultivar based on observations of nine-month-old specimens growing in the trial beds in full sun in Canby, Oreg. Canby is Zone 8 on the USDA Hardiness map. Temperatures range from a high of 95° F. in August to 32°

F. in January. Normal rainfall in Canby is 42.8 inches per year. The color descriptions are all based on The Royal Horticultural Society Colour Chart, 2007.

Plant:

*Type*.—Herbaceous perennial.

*Hardiness*.—USDA Zones 6 to 9.

*Size*.—60 cm wide and 50 cm tall to top of inflorescences.

*Form*.—Mound.

*Vigor*.—Excellent.

*Roots*.—Fibrous, stems root easily from stem cuttings.

Stem:

*Type*.—Ascending, well branched.

*Size*.—Grows to 30 cm tall to where branches for flowering and 8 mm wide.

*Number of stems from the crown*.—About 6.

*Branching habit*.—Freely branched.

*Internode length*.—3.5 cm to 4.5 cm.

*Surface*.—Glabrous.

*Color*.—Brown 200A at bottom 7 cm blending to Yellow Green 147B.

Leaf:

*Type*.—Simple.

*Shape*.—Pinnately 5-parted with thread-like segments, to linear on top leaves.

*Arrangement*.—Opposite.

*Size*.—Thread-like segments can spread to 8.5 cm wide and 5.5 cm long, the terminal linear segment can grow to 40 mm long and 3 mm wide, laterals can grow to 47 mm long and 3 mm wide.

*Apex*.—Acute.

*Margins*.—Entire.

*Petiole*.—2 mm to 11 mm long and 1 mm wide, Green N137A.

*Surface texture*.—Sparsely pubescent on top and bottom side.

*Venation*.—Pinnate, visible main vein the same color as the leaf on both sides.

*Color*.—Topside Green N137A, bottom side Green N137C.

Inflorescence:

*Type*.—Long stalked terminal heads of daisy type inflorescences.

*Peduncle*.—Grows to 4.5 cm long, 1 mm wide, glabrous, Green 137A.

*Size*.—Grows to 3.5 cm wide and 11 mm deep.

"*Flower bud*".—Globular, 4 mm wide and 5 mm deep, Yellow Green147B on sides and Greyed Orange 164B on top, glabrous.

*Receptacle*.—Disc shaped, 3 mm wide and 1.5 mm deep, Green 148B.

*Phyllaries*.—In 2 series; first series closet to ray florets, campanulate, 5 mm deep and spreading 8 wide mm wide, 8 in number, each 4 mm long and 3 mm wide, triangular, tip acute and reflexed, margin entire, glabrous on both sides, both sides Greyed Yellow 164A at the top ⅓ blending to 161A in middle blending to 147A on bottom ⅓; lower series in an area 3 mm deep and 5 mm wide, 8 linear lobes, 2 mm long and 1 mm wide, margin entire, tip acute, top side glandular, both sides glabrous and Green 147A.

*Lastingness*.—Each inflorescence lasts about a week on the plant.

Florets:

*Type*.—Composite.

*Ray florets*.—8 in number (with 0 to 3 linear upright smaller florets, 4 mm to 5 mm long and 1.5 mm to 2 mm wide) with no pistil or stamen, grows to 15 mm long, 8 mm wide, obovate, slightly reflexed, with the tip obtuse and shallowly notched, base cuneate, margins entire, glabrous on both sides; topside Yellow 2D on top half blending to 4C at the base, bottom side Yellow 4D on top half to Yellow 4C on bottom half.

*Disc*.—Flat becoming rounded with maturity, 6 mm wide and becoming 3 mm deep with maturity, Greyed Purple 187B.

*Disc florets*.—Tubular, with stamen and pistil, about 35 in number, 8 mm long and 1 mm wide, tubular; corolla 5 mm long, 5 lobed, tube Yellow 6C, lobes Greyed Purple 187B; pistil 1, 8 mm long, ovary 3 mm long, Green Yellow 1C, style 4 mm long, with extruding, 2-branched stigma, stigma and style Yellow Orange 16A; stamen 5, anthers 1.2 mm long, Greyed Brown N199B, pollen Yellow 5A.

*Bloom period*.—June through frost in Canby, Oreg.

*Fragrance*.—Slight.

*Seed*.—None seen.

*Fertility*.—Unknown.

Disease and pests: No pests or diseases have been observed on plants grown under commercial conditions in Canby, Oreg. No resistances are known.

I claim:

1. A new and distinct *Coreopsis* plant as herein illustrated and described.

* * * * *

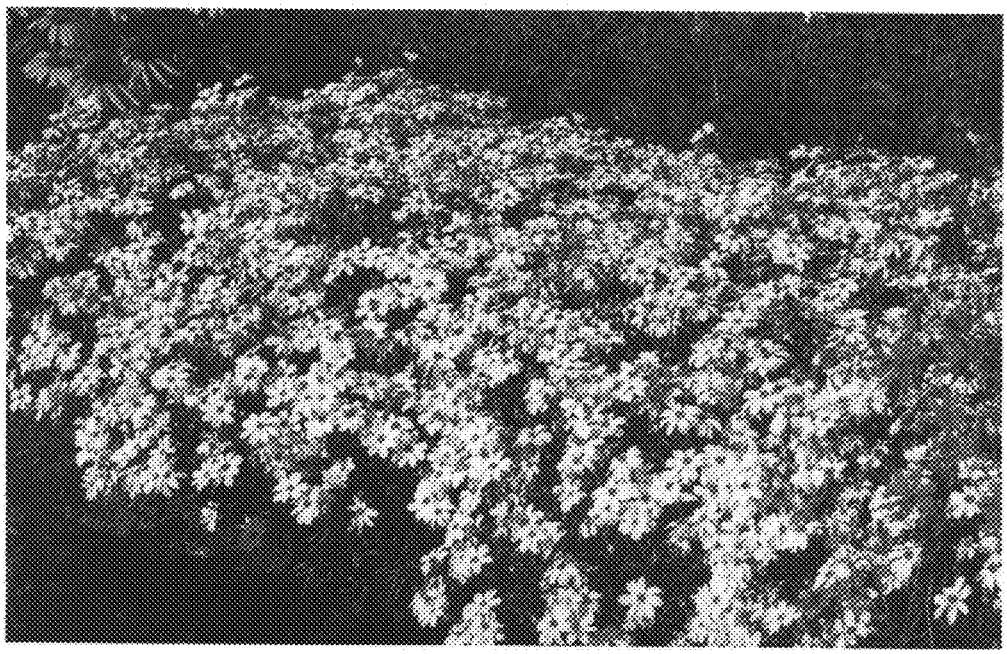
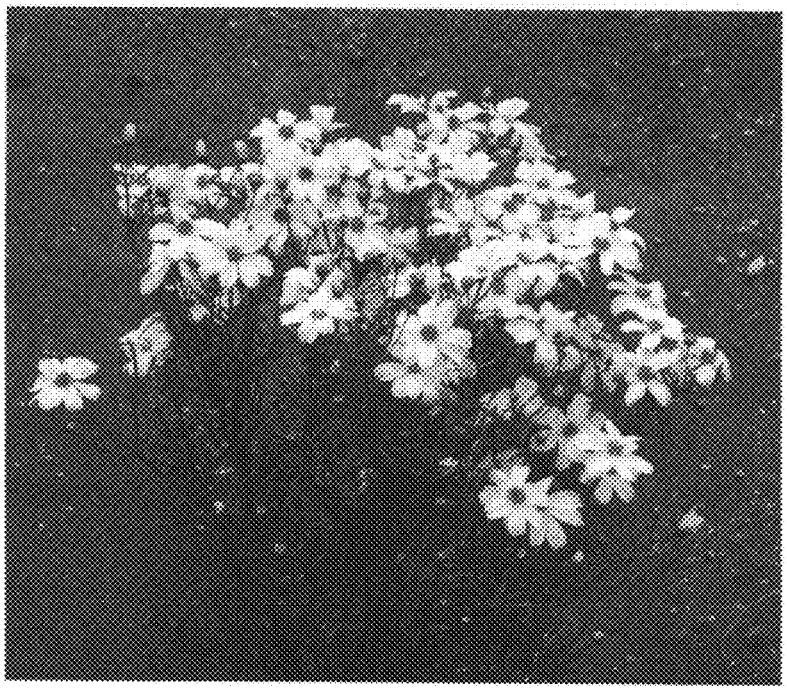
FIG. 1 above,
FIG. 2 on left